(12) United States Patent
Drobe et al.

(10) Patent No.: US 8,721,082 B2
(45) Date of Patent: May 13, 2014

(54) CHARACTERIZATION OF A PERCEPTION OF BLUR

(75) Inventors: Björn Drobe, Charenton-le-Pont (FR); Guillaume Giraudet, Charenton-le-Pont (FR)

(73) Assignee: Essilor International (Compagnie Generale d'Optique, Charenton-le-Pont (FR)

( * ) Notice: Subject to any disclaimer, the term of this patent is extended or adjusted under 35 U.S.C. 154(b) by 54 days.

(21) Appl. No.: 13/381,205

(22) PCT Filed: Jun. 25, 2010

(86) PCT No.: PCT/FR2010/051319
§ 371 (c)(1),
(2), (4) Date: Dec. 28, 2011

(87) PCT Pub. No.: WO2011/001082
PCT Pub. Date: Jan. 6, 2011

(65) Prior Publication Data
US 2012/0106813 A1 May 3, 2012

(30) Foreign Application Priority Data
Jun. 29, 2009 (FR) ...................................... 09 54408

(51) Int. Cl.
*A61B 3/02* (2006.01)
*A61B 3/032* (2006.01)
(52) U.S. Cl.
CPC ....................................... *A61B 3/032* (2013.01)
USPC ............................ 351/237; 351/238; 351/246

(58) Field of Classification Search
CPC ....... A61B 3/028; A61B 3/0285; A61B 3/032
USPC .................................................. 351/222–247
See application file for complete search history.

(56) References Cited

U.S. PATENT DOCUMENTS

| 4,365,873 | A | 12/1982 | Ginsburg |
| 6,325,508 | B1 | 12/2001 | Decreton et al. |
| 2004/0174499 | A1 | 9/2004 | Toshima et al. |
| 2007/0115432 | A1* | 5/2007 | Thibos .......................... 351/246 |
| 2008/0165324 | A1* | 7/2008 | Lindacher et al. ............ 351/233 |

OTHER PUBLICATIONS

Akutsu, H. et al., "Recognition Thresholds for Letters with Simulated Dioptric Blur," Optometry and Vision Science 77 (10):524-530, Oct. 2000.

(Continued)

*Primary Examiner* — Darryl J Collins
*Assistant Examiner* — Gary O'Neill
(74) *Attorney, Agent, or Firm* — Seed IP Law Group PLLC

(57) ABSTRACT

The invention relates to a method for characterizing a perception of blur by a subject (10) in order to determine a dioptric blur value for an image (C) observed by the subject. The image has a blur generated by the low-pass filtering of the image components in accordance with the respective space frequencies of said image components. An indication of the perception thereof of blur in the image is provided by the subject and is associated with the dioptric blur value. Several images associated with different dioptric blur values are used for defining a dioptric blur threshold value for the subject that corresponds to a blur perception criterion. The invention can be used for adjusting the design of a progressive lens for the subject in accordance with the sensitivity to said visual blur of said object.

15 Claims, 2 Drawing Sheets

(56) References Cited

OTHER PUBLICATIONS

Figure 1:
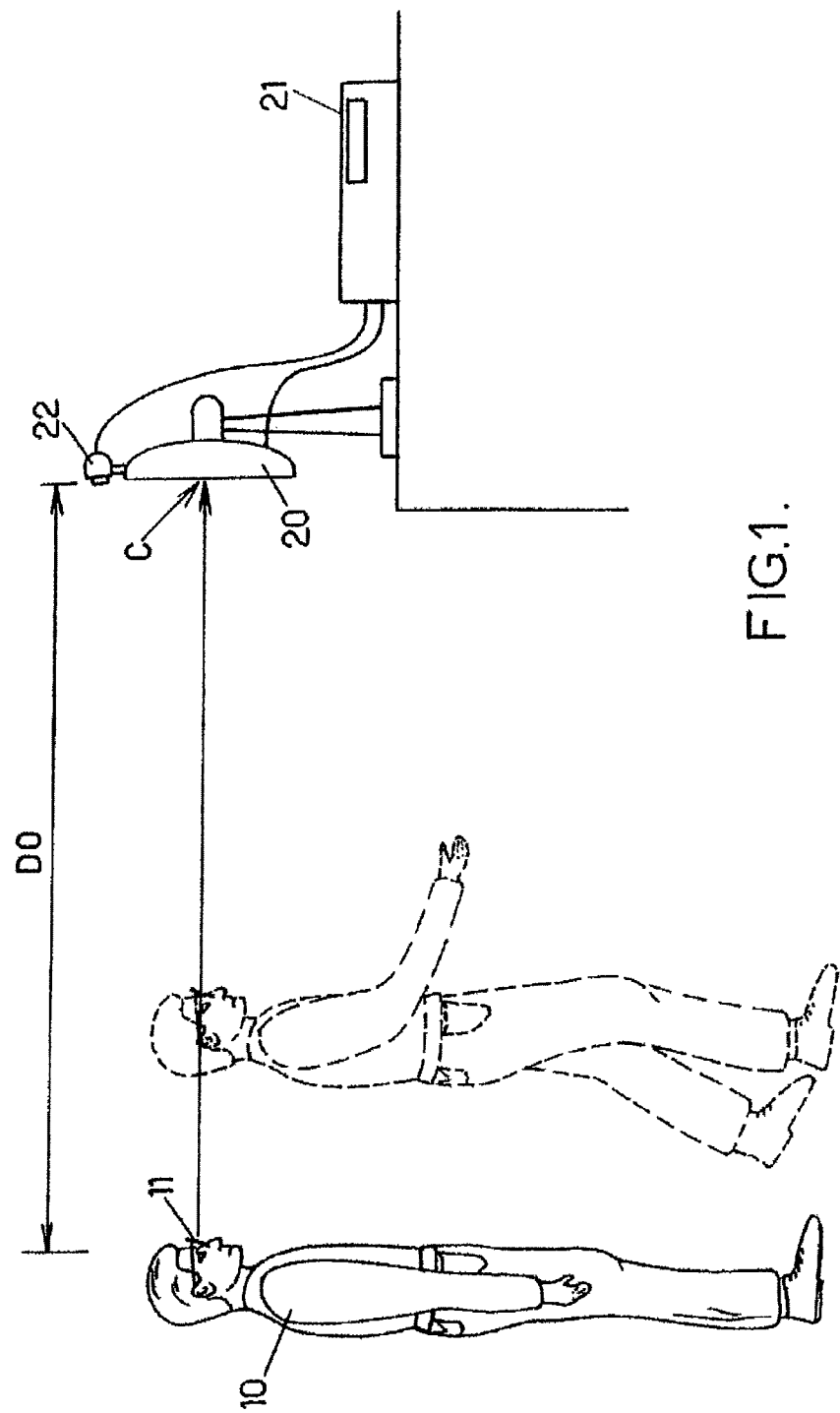

Ciuffreda et al. "'Bothersome blur': A functional unit of blur perception," *Vision Research* 46:895-901, 2006, 7 Pages.

Legge et al. "Tolerance to visual defocus," *J. Opt. Soc. Am. A* 4(5):851-63, May 1987, 13 Pages.

Legras et al. "A method for stimulation of foveal vision during wear of corrective lenses," *Optometry and Vision Science* 81(9):729-38, Sep. 2004, 10 Pages.

Schmid et al. "Blur detection thresholds in childhood myopia: single and dual target presentation," *Vision Research* 42:239-47, 2002, 9 Pages.

Tulet et al. "Etude préliminaire de l'influence des fréquencies spatiales sur l'apparence couleur," *COmpression et REprésentation des Signaux Audiovisuels*, Nov. 2006, 5 Pages.

* cited by examiner

CHARACTERIZATION OF A PERCEPTION OF BLUR

The present invention relates to a method for characterizing a perception of blur by a subject, as well as a device suitable for implementing such a method.

It is known that a difference between the ametropia of a spectacles wearer and the ophthalmic correction provided by a spectacle lens used by this wearer produces a hazing of his vision called "dioptric blur". When this dioptric blur results from a defocusing of the image on the back of the retina, it is spontaneously overcome by an accommodation of the eye of the wearer, subject to "accommodation lag" and providing that the limit of ocular accommodation of the wearer is not exceeded. Nevertheless, this results in visual fatigue for the wearer. Generally, aside from the ocular accommodation faculty, dioptric blur constitutes a vision defect of a spectacles wearer.

Progressive spectacles lenses allow a presbiopic wearer to see sharply at variable distances through a far-vision zone of the lens, a near-vision zone, and through a channel linking the far-vision and near-vision zones. Outside these zones, however, they show variations of optical power and astigmatism which give rise to dioptric blur for the wearer. Such progressive lenses are thus designed to produce a trade-off between the width of the field of view in which the optical power and astigmatism of the lens correspond to the ophthalmic prescription issued for the wearer, and a dioptric blur which remains limited for the directions of gaze that pass through the lens outside the far-vision and near-vision zones. In particular, the dioptric blur outside the far-vision and near-vision zones of a progressive lens increases with an increase in the addition value of this lens. It is noted that the addition of a progressive lens is the difference between the optical power values of this lens respectively for a near-vision reference direction and a far-vision reference direction.

Moreover, numerous physiological studies have shown that the visual perception of blur is very variable between different subjects. Thus, two spectacles wearers having identical ophthalmic prescriptions and fitted with spectacles lenses that are also identical can have a different discomfort experience of the dioptric blur produced by these lenses, for certain oblique directions of their gaze. For example, a first wearer may report experiencing discomfort from this blur while a second wearer may confirm satisfactory visual comfort. The compromise made by these identical lenses between their ophthalmic function and the residual dioptric blur that they produce is then suitable for the second wearer, and must be modified for the first. It is therefore necessary to take account of the sensitivity of each wearer to the perception of blur when prescribing a progressive lens for this wearer.

To this end a test is required which makes it possible to obtain from a subject his assessment of the perception of blur under identified conditions. It would then be sufficient in principle to provide him with a spectacles lens producing dioptric blur values below a threshold value for which he had stated that this level of blur was acceptable. But several difficulties then arise for the subject in carrying out a blur perception test:

- the sharpness perceived by the subject for an image shown to him depends on his distance from the image. In fact, the further the subject is from the image, the less its details appear blurred, as they become too small to be visible;
- the perception of blur is partially subjective, as it can be influenced by a sensation of constraint or freedom of movement of the subject during the test. In particular, the freedom of the subject to move further from or nearer to an image of which blur is to be assessed is important;
- a perception test of an actual dioptric blur would consist of the assessment by the subject of blur resulting from defocusing of an optical system through which he was observing an image. However, such a test is awkward to implement and imposes constraint on the subject. In fact, during the test the subject would be required to look through the optical system, which does not reproduce the vision conditions of daily life. In particular, his field of view would be restricted transversally by the optical system, constituting a limitation capable of significantly altering his perception of blur; and
- the pupil diameter is involuntarily involved in the perception of blur, as it determines a cross section of the light beams that converge imperfectly on the retina from a point of the image viewed. However, this pupil diameter varies according to the ambient brightness.

But, the adoption of a threshold value for dioptric blur that is too low, below which blur is considered to be acceptable for a future spectacles lenses wearer, is likely to result in spectacles lenses being supplied which have other characteristics that are unnecessarily degraded in a trade-off between blur and these other characteristics. For example, the quality of dynamic vision through a progressive spectacles lens can be reduced, in order to obtain a dioptric blur which remains low in broader fields of the lens.

The present invention thus aims to achieve the following goals.

A first aim of the invention is provide a test of perception of blur by a subject which provides a reliable result.

A second aim of the invention consists of obtaining an assessment by the subject of the blur that he perceives when viewing an image, in a manner which is coherent with an optical determination of this blur.

A third aim of the invention is to provide a test of the perception of blur by the subject, the result of which is representative of a perceived sensation of blur that the subject would experience in daily life.

A fourth aim of the invention is to provide a blur perception test which is easy to use and inexpensive.

To this end, the invention proposes a method for characterizing a perception of blur by a subject, comprising the following steps:

/1/ selecting a blur perception criterion which allows a blur limit to be established on the basis of which the criterion is met or not for the subject;

/2/ generating, then displaying, an image on a display screen, this image having a blur which corresponds to a low-pass filtering of image components with respect to space frequencies of these image components;

/3/ for the subject, while he is free to move further from or nearer to the display screen, thereby varying a distance of observation: observing the displayed image and reporting if the blur perception criterion selected in step /1/ is met or not;

/4/ selecting a value for the distance of observation achieved by the subject at least one moment during step /3/;

/5/ determining, from the value selected in step /4/ for the distance of observation, a cut-off space frequency of the low-pass filtering of the displayed image and optionally a pupil diameter value, a dioptric blur value for the displayed image when it is observed by the subject, this value being associated with the report provided by the subject in step /3/ for responding to the perception of blur criterion.

Moreover, the dioptric blur value determined in step /5/ is a decreasing function of the value selected for the distance of observation when the cut-off space frequency is constant, for the low-pass filtering of the displayed image.

Thus, in a method according to the invention, the dioptric blur value is determined on the basis of a cut-off space frequency of the low-pass filtering of the components of the displayed image, and a value of the distance of observation adopted by the subject. Optionally, a value for his pupil diameter may also be taken into account. In this way, the method provides an assessment by the subject of his perception of blur which is correlated with a dioptric blur value established while taking account of the conditions of the perception test. In other words, the assessment of the perception of blur of the image by the subject is assigned a blur quantification value having an optical significance. It is then possible to compare the dioptric blur value determined by a method according to the invention for a subject, to dioptric blur values calculated for a spectacles lens, or to a dioptric blur value determined for another subject, also using a method according to the invention.

In particular, the dioptric blur value determined in step /5/ may be inversely proportional to the value selected in step /4/ for the distance of observation, when the cut-off space frequency of the low-pass filtering of the displayed image is constant.

The low-pass filtering of the displayed image is characterized by the cut-off space frequency of the components of the image, when this image is broken down into a combination of such components which together reconstitute the displayed image. In this case, the dioptric blur value determined in step /5/ may be inversely proportional to the cut-off space frequency of the low-pass filtering of the displayed image, when the value selected in step /4/ for the distance of observation is constant. In particular, it may be calculated by using the following formula:

$$B(\text{diopter}) = K/[DO(\text{meter}) \times FC(\text{meter}^{-1})] \quad (1)$$

where B is the dioptric blur value expressed in dioptres, DO is the distance of observation value expressed in meters, FC is the cut-off space frequency of the low-pass filtering of the displayed image, expressed in cycles per meter measured parallel to the screen, and K is a positive, non-zero proportionality coefficient.

Moreover, given that the subject is free to move in order to view the displayed image, he provides the report of his perception of blur of the image which is displayed, under conditions similar to those of daily life. In particular, the blur perception test method introduces few, or no, additional constraints compared with usual vision conditions, which would be capable of altering his assessment of his perception of blur. In particular, the field of view of the subject is not restricted transversally, as in the case of an optical instrument used for viewing the image.

Finally, the image displayed may be generated by a computer unit, for example by using digital filtering. The display screen can then be controlled by this computer unit. Generally, the method of the invention can be carried out by using normal inexpensive and compact devices. Moreover, it is quite quick for the subject to carry out. It is therefore particularly suitable for use in a retail sales outlet for ophthalmic spectacles lenses, such as an optician's practice.

The blur perception criterion used in a method according to the invention makes it possible to characterize the perception of blur as it is assessed by the subject. For example, this may be a blur detection criterion, a criterion of visual discomfort caused by blur, or a criterion of loss of legibility of at least one alphanumeric character contained in the displayed image.

Finally, the pupil diameter value optionally used in step /5/ may result from a measurement carried out on the subject.

The invention moreover proposes a device suitable for characterizing a perception of blur by a user, this device comprising:
 a system for generating images each having a blur corresponding to a low-pass filtering of image components with respect to space frequencies of these image components;
 a screen, suitable for displaying the images generated by the image generation system;
 a data processing unit, suitable for determining a dioptric blur value from a distance of observation value adopted by the user for observing an image displayed on the screen, a cut-off space frequency of the low-pass filtering of the displayed image, and optionally a pupil diameter value.

Such a device can be used for characterizing the perception of blur by a subject according to a method such as described previously. Moreover, it can be compact and inexpensive.

Figure 2:
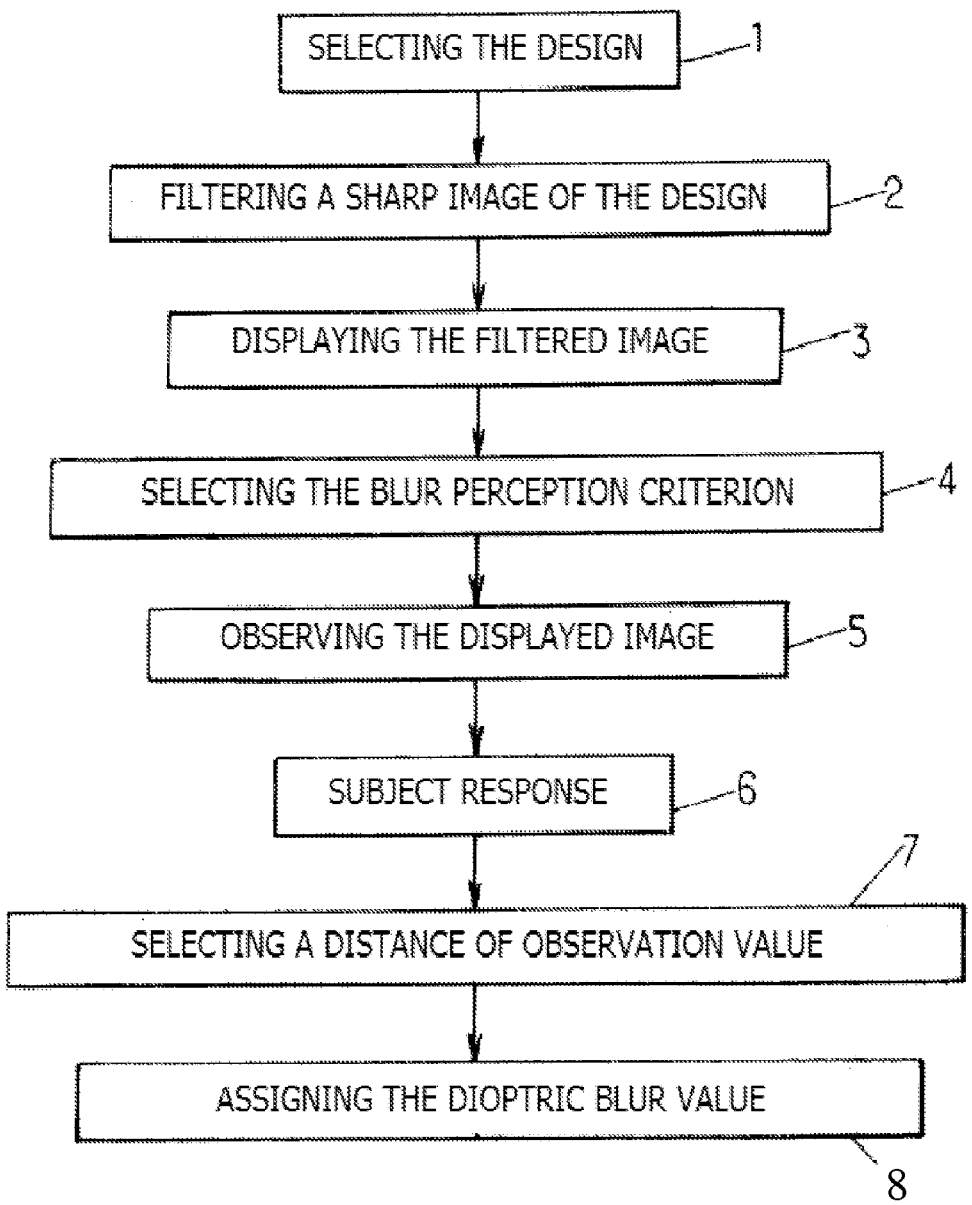

Other features and advantages of the present invention will become apparent from the following description of non-limitative embodiment examples, with reference to the drawings now described:

FIG. 1 shows an implementation of a characterization of perception of blur according to the invention; and FIG. 2 is a synoptic diagram of the steps of a method according to the invention.

A device for the characterization of a perception of blur by a subject 10 can comprise a computer unit 21 and a screen 20. Advantageously, the unit 21 is suitable for selecting and/ or calculating images, controlling a display of these images on the screen 20, and determining a dioptric blur value corresponding to the displayed image while taking account of observation parameters, including the distance of observation between the subject 10 and the screen 20. Preferably, the screen 20 is located at eye level of the subject 10.

Advantageously, the device comprises moreover a distance measurement system, arranged for measuring the distance of observation, marked DO in the figure. Any distance measurement systems can be used, but the distance measurement system used is preferably suitable for measuring the distance of observation DO without a continuous material link between the screen 20 and the user 10, and optionally with a continuous sequence of measurements. In this way, the distance of observation DO can be measured during the procedure without creating constraints for the subject 10. Moreover, it may be measured without the subject 10 being aware of it, so that he is physically and psychologically freer in his movements in relation to the screen 20. The following systems allow in particular simple and comfortable implementation of the invention:
 a graduated scale that may be marked on the floor starting from a vertical direction, passing through the screen 20, parallel to which the subject 10 can move by walking forward or backward, in order to move nearer to or further from the screen 20;
 an ultrasound-based telemetry system, using infra-red radiation or a laser beam which may comprise a transmitter and/ or a sensor arranged at the level of the screen 20 in the direction of the subject 10; or
 an optical distance-measurement system.

Such distance measurement systems are well known to a person skilled in the art, so it is unnecessary to describe them here. Optionally, some of these systems may comprise one or more transmitters, sensors or reflectors worn by the subject 10. Such transmitters/ sensors/ reflectors may in particular be incorporated into a spectacles frame 11 provided to the subject 10. The system for measuring the distance of observation DO may be linked to the computer unit 21, so that the result of each measurement can be used directly for determining the dioptric blur value.

Optionally, the device for characterizing the perception of blur may comprise moreover a system for measuring a pupil diameter of the user 10. Such systems producing measurements of the diameter of at least one of the pupils of the subject 10 are also known to a person skilled in the art. They may be incorporated into the pair of spectacles 11 which may be provided for the subject 10, or comprise a camera remotely producing an enlarged image of at least one of the eyes of the subject 10. In the latter case, image processing can then automatically identify each pupil of the subject 10 in the captured images, and determine the diameter of the pupil in real time. DP hereinafter denotes the pupil diameter. Advantageously, the distance measurement system and the pupil diameter measurement system may be adapted to simultaneously carry out the measurements of the distance of observation DO and the diameter of the pupil DP of the user 10, at a same time. In the implementation of the invention shown in FIG. 1, the two measurement systems are combined by using a video camera 22 arranged on the screen 20, and suitable reflectors borne by the frame of the pair of spectacles 11.

When the device for characterizing the perception of blur does not comprise a measurement system of the pupil diameter the user 10, a fixed value for the diameter DP may be adopted, for example equal to 2 mm (millimeter). In this case in particular, the ambient brightness as well as the brightness of the images displayed on the screen 20 are advantageously fixed in order to reduce the variations in the pupil diameter of the subject 10 during the characterization of his perception of blur.

It is not essential for the spectacles 11 which may be provided for the subject 10 while the procedure is carried out, to produce an ametropia correction. Such an ametropia correction may be absent when the ametropia diagnosed for the subject 10 is itself low. Conversely, the at least partial correction of the ametropia of the subject 10 by the spectacles 11, during the characterization of his perception of blur, may be necessary when the ametropia of the subject 10 is significant. In this case, the lenses of the pair of spectacles 11 are preferably monofocal. The ametropia correction provided to the subject 10 during the characterization of his perception of blur may then be deduced from the dioptric blur value determined from the displayed image on the screen 20, the distance of observation DO and optionally the diameter of the pupil DP.

The procedure for characterizing the perception of blur by the subject 10 is now described, with reference to FIG. 2.

An image is generated, containing a design affected by a display blur. Firstly, the design is selected (step 1), which may be an alphanumeric character C. Display blur is then introduced into the image by performing out low-pass filtering of a sharp image of the design C (step 2). Such filtering may be carried out in analog fashion by means of the signals for displaying on the screen 20. Preferably, it is carried out digitally by the computer unit 21 from the display data of the design C.

Such low-pass filtering is equivalent to a breakdown of the sharp image of the design C into image components which correspond to varying space frequencies, followed by reducing the amplitudes of the image components having high space frequencies. The principle of such filtering is known, and in particular that the filtering may have an attenuation coefficient of the image components which varies in different ways as a function of the space frequencies. The image displayed is the recombination of the image components thus attenuated. The design C then has a diffuse contour in the displayed image, through which the contrast varies progressively from the inside of the design towards the outside of the design, producing a display blur. Such blur is actual in the displayed image, as opposed to the dioptric blur produced in the eye when the subject views a sharp image. One of the aims of the invention consists of establishing a relationship between the actual blur of an image, which is generated voluntarily, and dioptric blur. Indeed, display blur is easier to produce in a controlled manner than blur resulting from a discrepancy in the adjustment of an optical instrument.

In a known manner, a low-pass filtering applied to an image can be characterized by a cut-off space frequency. The image components are then attenuated when their respective space frequencies are greater than the cut-off space frequency, and are not significantly attenuated when their respective space frequencies are below the cut-off space frequency. The cut-off space frequency then determines the minimum distance in the filtered image, for the separation between two details of the design C which can be identified separately from each other. Below this minimum separation distance, the details appear confused in the filtered image.

The breakdown of the image into image components identified by their respective space frequencies may be a two-dimensional Fourier transform. Other types of image breakdown may alternatively be used, such as breakdown into "wavelets", known to a person skilled in the art.

The filtered image may either be calculated in real time so that the subject 10 performs the characterization of his perception of blur according to the invention, or have been calculated in advance, then stored in an image library for different low-pass filtering space frequency cut-off values. In the second case, the displayed image is selected from the library as a function of the design and filtering.

The filtered image of the design C is displayed on the screen 20 (step 3).

The subject 10 adopts a position in front of the screen 20. An operator then asks him to view the displayed image and to report the level of blur with which he visually distinguishes the design C. This blur level is assessed according to a blur perception criterion selected by the operator and communicated to the subject 10 (step 4). This criterion may be one of the following, given by way of example only:

can blur in the displayed image be perceived or not by the subject 10?

does blur cause visual discomfort to the subject 10, during observation of the displayed image?

is the subject 10 able to read the alphanumeric character C?

These three criteria are therefore, in order: detection of blur, discomfort experienced and a loss of legibility. Optionally, these perception criteria can be supplemented by others in order to obtain a more detailed characterization of the perception of blur by the subject 10.

The subject 10 is free to move nearer to or further from the screen 20 when he observes the displayed image (step 5). In this way, he can adopt a position at a distance from the screen 20 which corresponds to a condition of observation which is habitual for him. He can thus reproduce the vision conditions that are most frequent for him in daily life. He can also adopt a position at a distance from the screen 20 which corresponds to his greatest feeling of comfort. In fact, the choice of the distance of observation DO by the subject 10 is also unconsciously influenced by environmental parameters such as the dimensions of the room in which the blur perception test is carried out, the degree of crowding of the room, the ambient brightness, the colour of the walls, designs present on the walls, contrast between such wall designs, the brightness of the displayed image, the design and the shades of this image, etc. For this reason it is therefore advantageous to select a psychophysical method of visual perception, which makes it possible to reduce the effect of such environmental parameters on the result of the blur perception characterization. Such psychophysical methods are described in available articles or publications, so it is unnecessary to present them again here.

The distance of observation DO may be measured continuously while the subject 10 observes the displayed image.

The subject 10 then answers the question for at least one of the blur perception criteria, in order to characterize the level of blur that he perceives in the image displayed on the screen 20 (step 6).

A value for the distance of observation DO is then selected, which was adopted by the subject 10 (step 7). This selection may be performed in various ways, including:

the selected value may correspond to the shortest distance of observation achieved by the subject 10 at least one moment during his observation of the displayed image; and the selected value may correspond to a distance of observation reported by the subject 10 as providing him with maximum comfort when observing the displayed image.

A value for the diameter of the pupil DP may also be selected. This may be a reference value, for example 2 mm, or a value measured on the subject 10. Preferably, the diameter of the pupil DP is measured on the subject 10 continuously while he observes the displayed image, and the value of this selected diameter DP may correspond to the same moment as the distance of observation DO which was also selected.

The invention then makes it possible to attribute a dioptric blur value to the situation of observation of the displayed image as it is viewed by the subject 10 (step 8). Each answer of the subject 10 to the question of one of the blur perception criteria, when combined with the dioptric blur value, characterizes the perception of blur by the subject 10.

Generally according to the invention, this dioptric blur value is a decreasing function of the selected distance of observation DO, when the dioptric blur is expressed as a function of this distance of observation DO and of the cut-off space frequency FC. Indeed, the diffuse contour of the design C in the displayed image becomes more visible by the subject 10 as the distance of observation DO becomes greater. In particular, the dioptric blur value determined according to the invention may be inversely proportional to the selected value for the distance of observation DO.

This dioptric blur value may also be inversely proportional to the cut-off space frequency FC of the low-pass filtering of the displayed image.

In this case, the dioptric blur value of the displayed image, marked B, may be determined according to a formula of the following type:

$$B(\text{diopter}) = K / [DO(\text{meter}) \times FC(\text{meter}^{-1})] \quad (1)$$

K being a non-zero positive proportionality coefficient.

Moreover, the cut-off space frequency FC of the filtered image is a number of cycles of variation of the intensity of the image component, per unit of a length measured parallel to the screen 20. It may be converted into a number of cycles NC per degree of angular separation of variation of the direction of gaze of the subject 10, according to the following formula:

$$FC(\text{meter}^{-1}) = NC(\text{cycles/degree}) \times 180 / (\pi \times DO) \quad (2)$$

By combining formulae (1) and (2), we have:

$$B(\text{diopter}) = K' / NC(\text{cycles/degree}) \quad (3)$$

where $K' = K \times \pi / 180$. In other words, under the conditions set out above, the dioptric blur is inversely proportional to the number of cycles NC per degree of angle of view for the subject 10, and becomes independent of the distance of observation DO. When the constant K' is equal to 0.25, the number NC of cycles per degree of angle of view corresponds to the visual acuity of the subject, according to Swaine, for a dioptric blur B which would be produced by spherical defocus.

According to an improvement of the invention, the dioptric blur may be determined more precisely by, in addition, taking account of the diameter of the pupil DP. The dioptric blur is then an increasing function of the pupil diameter value, in addition to its variations as a function of the distance of observation DO and the cut-off space frequency FC. When this blur is equivalent to spherical defocus, the equation (1) may be replaced by the following, with the non-zero first order variation as a function of the diameter of the pupil DP:

$$B(\text{diopter}) = K \times [1 + \alpha \cdot DP^2] / [DO(\text{meter}) \times FC(\text{meter}^{-1})] \quad (1')$$

where $\alpha$ is a positive coefficient. When the diameter of the pupil DP is expressed in millimeters, $\alpha$ may be taken to be equal to 0.055 mm$^{-2}$, for example.

Optionally, the image displayed, in particular the low-pass filtering applied thereto, may be adjusted while the subject 10 moves while staring at this image on the screen 20. For example, the cut-off space frequency FC may be modified as a function of the result of the real-time measurement of the distance of observation DO. Such a modification can compensate at least partially for the dioptric blur variation resulting from the movements of the subject 10. For example, the cut-off space frequency FC used for the displayed image may be modified in real time while the subject observes the latter, so as to keep the product of this cut-off space frequency FC and the distance of observation DO constant. In this case, the dioptric blur value obtained, with which the report of perception of blur given by the subject 10 according to the selected perception criterion is combined, is automatically compensated by the effect of the distance of observation DO.

More generally, the image generation system 21 may be suitable for generating the image to be displayed on the screen 20 in a variable manner as a function of at least one measurement result chosen from the value of the distance of observation DO and the pupil diameter value of the subject 10.

Finally, the steps of generating and displaying the image on the screen 20, observation of the latter by the subject 10 while being able to move further or nearer, selecting a value for the distance of observation DO and determining a dioptric blur value may be repeated for the same blur perception criterion. In other words, the sequence of these steps may be performed several times while varying the cut-off space frequency of the low-pass filtering of the displayed image for successive executions of this sequence of steps. Then, when the subject 10 provides opposing reports in answer to the blur perception criterion for at least two executions of the sequence, a range for a threshold value of the dioptric blur which corresponds to this perception criterion can be deduced for the subject 10 from these reports, correlated with the corresponding determined dioptric blur values. This dioptric blur threshold value corresponds to the limit between positive and negative answers by the subject 10 to the perception criterion. It can then be used for adjusting the dioptric blur of an ophthalmic correction lens provided for the subject. When this lens is of the progressive lens type, the dioptric blur threshold value obtained for the subject may be used to adjust the design of the lens supplied as a function of the sensitivity of the subject to visual blur.

It is understood that the invention can be implemented by modifying some aspects thereof in relation to the above description, while keeping some of the advantages mentioned. In particular, it is understood that the mathematical formulae given may be replaced by formulae characterizing different variations, although having identical variation signs, without changing the objects and advantages of the invention.

The invention claimed is:

1. A method for characterizing a perception of blur by a subject, comprising:
   /1/ selecting a blur perception criterion allowing a blur limit to be established on the basis of which the criterion is met or not for the subject;
   /2/ generating and displaying an image on a display screen, said image having a blur corresponding to a low-pass filtering of image components with respect to space frequencies of said image components;
   /3/ receiving from the subject, said subject being free to move further from or nearer to the display screen thereby varying a distance of observation, a report of whether the blur perception criterion selected in step /1/ is met or not when the subject observes the displayed image;
   /4/ selecting a value for the distance of observation achieved by the subject during step /3/;
   /5/ determining, from the value selected in step /4/ for the distance of observation and from a cut-off spatial frequency of the low-pass filtering of the displayed image, a dioptric blur value for the displayed image observed by the subject, said dioptric blur value being associated with the report received from the subject in step /3/ for responding to the perception of blur criterion, and said dioptric blur value being a decreasing function of the value selected for the distance of observation when a cut-off spatial frequency of the low-pass filtering of the displayed image is constant.

2. A method according to claim 1, wherein the dioptric blur value determined in step /5/ is inversely proportional to the value selected in step /4/ for the distance of observation, when the cut-off spatial frequency of the low-pass filtering of the displayed image is constant.

3. A method according to claim 1, wherein the dioptric blur value determined in step /5/ is inversely proportional to the cut-off spatial frequency of the low-pass filtering of the displayed image when the value selected in step /4/ for the distance of observation is constant.

4. A method according to claim 1, wherein the distance of observation of the displayed image by the subject is measured continuously during step /3/.

5. A method according to claim 1, wherein the value selected in step /4/ for the distance of observation corresponds to the shortest distance of observation achieved by the subject during step /3/.

6. A method according to claim 1, wherein the value selected in step /4/ for the distance of observation is reported by the subject as providing a maximum comfort of observation of the displayed image to said subject.

7. A method according to claim 1, wherein the sequence of steps /2/ to /5/ is carried out several times while varying the cut-off spatial frequency of the low-pass filtering of the displayed image for successive executions of said sequence of steps, so that opposing reports are received from the subject in step /3/ for responding to the blur perception criterion for at least two executions of said sequence of steps,
   and wherein a range for a dioptric blur threshold value corresponding to said perception criterion is deduced for the subject from the opposing reports provided by said subject and correlated with the dioptric blur values determined during the corresponding executions of step /5/.

8. A method according to claim 1, wherein the determining includes determining the dioptric blur value based also on a pupil diameter value that is obtained from a measurement performed on the subject.

9. A method according to claim 8, wherein the pupil diameter is measured on the subject continuously during step /3/, and wherein the value of said pupil diameter used in step /5/ corresponds to a same moment as the distance of observation selected in step /4/.

10. A device for characterizing a perception of blur by a user, comprising:
    a system configured to generate images each having a blur corresponding to a low-pass filtering of image components with respect to spatial frequencies of said image components;
    a screen configured to display the images generated by the system; and
    a data processing unit configured to determine a dioptric blur value from a value for a distance of observation from the screen to the user when the user is observing an image displayed on the screen and from a cut-off space frequency of the low-pass filtering of the displayed image.

11. A device according to claim 10, comprising a distance measurement system configured to measure the distance of observation between the user and the screen.

12. A device according to claim 11, in which the distance measurement system used is configured to measure the distance of observation without a continuous material link between the screen and the user.

13. A device according to claim 10, comprising a pupil measurement system configured to measure a pupil diameter of the user.

14. A device according to claim 13, comprising a distance measurement system configured to measure the distance of observation between the user and the screen, in which the distance measurement system and the pupil diameter measurement system are configured to simultaneously carry out the measurements of the distance of observation and the pupil diameter of the user.

15. A device according to claim 11, in which the image generation system is configured to generate the image to be displayed on the screen in a variable manner as a function of a measurement result of the distance of observation.

* * * * *